United States Patent [19]

Tseng

[11] Patent Number: 5,073,570

[45] Date of Patent: Dec. 17, 1991

[54] MONO-IODOPROPARGYL ESTERS OF DICARBOXYLIC ANHYDRIDES AND THEIR USE AS ANTIMICROBIAL AGENTS

[75] Inventor: Chuen-Ing J. Tseng, Edison, N.J.

[73] Assignee: Lonza Inc., Fair Lawn, N.J.

[21] Appl. No.: 311,523

[22] Filed: Feb. 16, 1989

Related U.S. Application Data

[63] Continuation-in-part of Ser. No. 244,060, Sep. 14, 1988, abandoned.

[51] Int. Cl.⁵ .............. A61K 31/235; A61K 31/225; C07C 69/80; C07C 67/08
[52] U.S. Cl. ........................ 514/533; 514/529; 514/547; 560/87; 560/98; 560/127; 560/197; 560/204
[58] Field of Search ............. 560/87, 98, 127, 197, 560/204; 514/529, 533, 547

[56] References Cited

U.S. PATENT DOCUMENTS

| | | | |
|---|---|---|---|
| 3,793,293 | 2/1974 | Ray-Chaudhuri et al. | 560/197 X |
| 3,796,746 | 3/1974 | D'Alelio | 560/197 X |
| 3,823,183 | 7/1974 | D'Alelio | 560/197 |
| 4,107,122 | 8/1978 | Morgan et al. | 560/197 X |

Primary Examiner—Jose G. Dees
Assistant Examiner—Vera C. Clarke
Attorney, Agent, or Firm—Darby & Darby

[57] ABSTRACT

The new compositions of matter of the present invention comprise compounds having one of the following formulas:

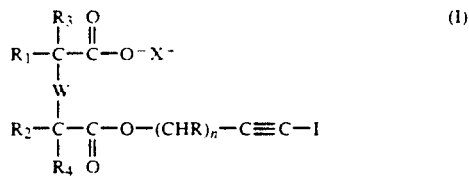

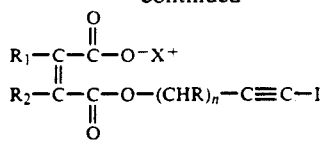

wherein:

R is hydrogen or methyl;

n is 1 to 16;

$R_1$ and $R_2$ are defined as $R_3$ and $R_4$ below or are joined to form a cycloalkyl, cycloalkenyl, aromatic or a heterocyclic ring containing an oxygen, nitrogen or sulfur atom or an alkoxy, amino, carboxyl, halo, hydroxyl, keto or a thiocarboxyl substituted derivative thereof;

$R_3$ and $R_4$ are independently selected from (A) hydrogen, alkyl, cycloalkyo, alkenyl, cycloalkenyl, aryl, a heterocyclic ring containing an oxygen, nitrogen or sulfur atom, alkoxy, amino, carboxyl, halo, hydroxyl, keto or a thiocarboxyl and (B) substituted derivatives of the alkyl, cycloalkyl, alkenyl, cycloalkenyl, aryl and the heterocyclic ring wherein the substitutions are alkyl, cycloalkyl, alkenyl, cycloalkenyl, aryl, alkoxy, amino, carboxyl, halo, hydroxyl, keto or a thiocarboxyl;

W may be a single bond, oxygen, $NR_5$, or $(CR_6R_7)_m$, wherein $R_5$ is hydrogen, alkyl, cycloalkyl, alkenyl, cycloalkenyl, aryl or a heterocyclic ring containing an oxygen, nitrogen or sulfur atom or a substituted derivative of alkyl, cycloalkyl, alkenyl, cycloalkenyl or aryl groups wherein the substitutions are alkyl, cycloalkyl, alkenyl, cycloalkenyl, aryl, alkoxy, amino, carboxyl, halo, hydroxyl, keto or a thiocarboxyl where $R_6$ and $R_7$ are defined as $R_3$ and $R_4$ above and m is an integer from 1 to 12; and X is hydrogen or a salt-forming cation.

Examples of such compositions are mono-iodopropargyl succinates, maleates, itaconates, diglycolates and phthalates. Other compounds include the mono-iodopropargyl esters of anhydrides such as dimethylglutaric anhydride and ethylenediamine tetraacetic dianhydride. They are used in microbiocidal formulations and effective microbiocides.

19 Claims, No Drawings

MONO-IODOPROPARGYL ESTERS OF DICARBOXYLIC ANHYDRIDES AND THEIR USE AS ANTIMICROBIAL AGENTS

This is a continuation-in-part of application Ser. No. 244,060 filed Sept. 14, 1988, now abandoned.

BACKGROUND OF THE INVENTION

The need for effective and economical antimicrobial compositions is well known. There are a wide variety of applications in industry, in the home, and in hospitals, where inhibiting the growth of microorganisms is necessary.

A class of compounds which have met with particular success because of their antimicrobial activity are the halopropargyl carbamates, particularly 3-iodo-2-propargyl butyl carbamate, IPBC. Processes for the preparation of such class of compounds and their use are disclosed in European Patent Application 0014032, published on Aug. 6, 1980, and U.S. Pat. Nos. 4,661,632, 4,639,541, 4,647,572 and 4,719,227. Unfortunately, such compounds often lack the necessary activity, light stability and/or solubility characteristics to facilitate formulation in both lipophilic and hydrophilic systems. This naturally imposes a severe limitation on the usefulness of these products.

BRIEF DESCRIPTION OF THE INVENTION

In accordance with the invention, it has now been discovered that mono-iodopropargyl esters of dicarboxylic anhydrides are new compositions of matter which are extremely useful as antimicrobial compositions for industrial, cosmetic and personal care product applications. Certain of these compounds are uniquely soluble in and readily miscible with lipophilic and hydrophilic systems, as for example the sodium salt. This is a distinct advantage over the prior compounds such as the commercially used 3-iodo-2-propargyl butyl carbamate, which is only modestly soluble in aqueous systems. In addition, the compositions of the invention have high activity and improved light stability.

A further embodiment of the invention is the preparation of the foregoing compounds by the reaction of iodopropargyl alcohols with a selected class of dicarboxylic acid anhydrides. The latter includes aliphatic, olefinic, aromatic and heterocyclic anhydrides, as for example succinic, maleic, phthalic, tetrachlorophthalic, diglycolic and itaconic anhydride.

A still further embodiment of the invention includes antimicrobial compositions containing these new compositions of matter and the use of such compositions.

DETAILED DESCRIPTION OF THE INVENTION

The new compositions of matter of the present invention comprise compounds having one of the following formulas:

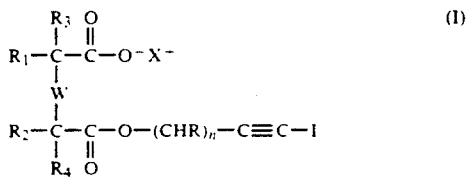

(I)

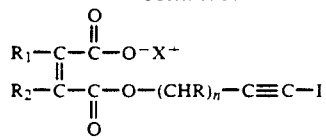

(II)

wherein:

R is hydrogen or methyl;

n is 1 to 16;

$R_1$ and $R_2$ are defined as $R_3$ and $R_4$ below or are joined to form a cycloalkyl, cycloalkenyl, aromatic or a heterocyclic ring containing an oxygen, nitrogen or sulfur atom or an alkoxy, amino, carboxyl, halo, hydroxyl, keto or a thiocarboxyl substituted derivative thereof;

$R_3$ and $R_4$ are independently selected from (A) hydrogen, alkyl, cycloalkyl, alkenyl, cycloalkenyl, aryl, a heterocyclic ring containing an oxygen, nitrogen or sulfur atom, alkoxy, amino, carboxyl, halo, hydroxyl, keto or a thiocarboxyl and (B) substituted derivatives of the alkyl, cycloalkyl, alkenyl, cycloalkenyl, aryl and the heterocyclic ring wherein the substitutions are alkyl, cycloalkyl, alkenyl, cycloalkenyl, aryl, alkoxy, amino, carboxyl, halo, hydroxyl, keto or a thiocarboxyl;

W may be a single bond, oxygen, $NR_5$, or $(CR_6R_7)_m$, wherein $R_5$ is hydrogen, alkyl, cycloalkyl, alkenyl, cycloalkenyl, aryl or a heterocyclic ring containing an oxygen, nitrogen or sulfur atom or a substituted derivative of alkyl, cycloalkyl, alkenyl, cycloalkenyl or aryl groups wherein the substitutions are alkyl, cycloalkyl, alkenyl, cycloalkenyl, aryl, alkoxy, amino, carboxyl, halo, hydroxyl, keto or a thiocarboxyl where R6 and R7 are defined as $R_3$ and $R_4$ above and m is an integer from 1 to 12. The above definition of $R_5$ includes, among other things, an aminoalkyl group.

The heterocyclic rings referred to in the above definitions may contain from 5 to 8 members, the alkyl or cycloalkyl groups from 1 to 18 carbon atoms, the alkenyl or cycloalkenyl groups from 2 to 18 carbon atoms, and the aryl groups from 6 to 10 members. X is hydrogen or a salt-forming cation such as an alkali metal, an alkaline earth metal, ammonium, tertiary ammonium, a quaternary ammonium, a biguanide or a polybiguanide.

In formula II, when $R_1$ and $R_2$ are hydrogen, the compound is a maleate. When $R_1$ and $R_2$ are joined together to form part of a six membered aromatic ring, the compound is a phthalate. In formula I, when $R_1$, $R_2$, $R_3$ and $R_4$ are hydrogen and W is a single bond, the compound is a succinate. When $R_1$, $R_2$, $R_3$ and $R_4$ are hydrogen and W is an oxygen, the compound is a diglycolate. Other compounds include the mono-iodopropargyl esters of anhydrides such as ethylenediamine tetraacetic dianhydride, 3,3-dimethylglutaric anhydride, S-acetylmercaptosuccinic anhydride, dichloromaleic anhydride, 2-dodecen-1-yl succinic anhydride and cis-5-norbornene-endo-2,3-dicarboxylic anhydride. Where hydrophilicity is desired, the sodium salts may be used because of their extremely high water solubility.

As noted above, preferred carboxylic acid anhydrides include succinic, itaconic, phthalic, tetrachlorophthalic and diglycolic anhydride.

The preparation of the compounds of the invention must be done with considerable care. The use of rigorous conditions or high reaction temperatures will cause undesirable side reactions.

The preferred method of preparing the compounds where a saturated acid anhydride is used includes dissolving both the alcohol and the anhydride component (e.g., succinic anhydride) separately in a non-alcoholic solvent (e.g., triethylamine or pyridine) and then admixing the solutions in the presence of a catalyst such as dibutyltin dilaurate at a reaction temperature of from −20° to 100° C., preferably from 0° to 60° C., and most desirably below 50° C. The reaction time typically is from 1 to 5 hours. The foregoing process is particularly useful for the reaction of iodopropargyl alcohol with acid anhydride such as succinic, phthalic and diglycolic anhydride. Near equimolar quantities of the alcohol and acid anhydride are used, it being imperative that the mono-substituted acid be formed.

With regard to the reaction of an unsaturated acid anhydride such as maleic anhydride, this may conveniently be carried out in a chloroform solution in the presence of a catalytic amount (e.g., from 0.1 to 5%) of a tertiary amine such as triethylamine. The reaction is carried out at or near room temperature. Examples of useful amines are triethylamine and other trialkylamines having from 1 to 18 carbon atoms, cyclic amines such as pyridine, picoline, N-methyl-piperidine, N,N-dimethylaminopyridine, N-methylmorpholine and quinoline and aryl-substituted amines such as triphenylamine.

In addition to the solvents set forth above, other non-alcoholic solvents may be used such as the halogenated organic solvents, e.g., the chlorinated alkanes, viz., carbon tetrachloride, methylene chloride, tetrachloroethylene; esters such as ethyl acetate; petroleum ethers, diethylether, tetrahydrofuran, toluene and dioxane.

The compositions of the invention have been found effective to inhibit the growth of bacteria, fungi and yeasts. Specifically, fungi and yeasts which may be inhibited include *Aspergillus niger, Candida albicans, Lentinus lepideus, Gloeophyllum trabeum, Corioulus versicolor, Trichoderma viride, Alternaria alternata, Pencillium decumbens, Botrytis cinerea, Colletotrichum cofeanum, Verticillium dahliae,* and *Trichophyton mentagrophytes.* Examples of the bacteria include *Salmonella choleraesuis, Serratia marcescens, Klebsiella pneumoniae, Enterobacter aerogenes, Aerobacter aerogenes, Bacillus subtilis, Proteus vulgaris, Streptococcus faecalis, Pseudomonas aeruginosa, Escherichia coli,* and *Staphylococcus aureus.*

The new iodopropargyl esters according to the invention can be used as active compounds for combating microorganisms, in particular for the preservation of cosmetics, personal care products, household products, and industrial materials such as adhesives, sizes, paper and cardboard, textiles, leather, wood, paints and articles made of plastic, cooling lubricants and other materials which can be attacked or decomposed by microorganisms. Components of production plants, for example cooling water, which can be impaired by multiplication of microorganisms, may also be mentioned in the context of the materials to be preserved. Also, the integrity of other water containing systems, such as swimming pools and spas, can be maintained by use of the materials of the invention. In addition, the materials of the invention can be used to control and eliminate microorganisms by disinfection and sanitization of surfaces such as found in homes, institutions and hospitals.

Examples of microorganisms which can effect contamination, degradation or a change in the industrial environments and materials are bacteria, fungi, yeasts, algae and slime organisms. The active compounds of the invention preferentially act against fungi, in particular mold fungi, fungi which discolor and destroy wood (Basidiomycetes), and against slime organisms and algae.

Microorganisms of the following genera are examples: Alternaria, such as *Alternaria tenuis,* Aspergillus, such as *Aspergillus niger,* Chaetomium, such as *Chaetomium globosum,* Coniophora, such as *Coniophora puteana,* Lentinus, such as *Lentinus tigrinus,* Penicillium, such as *Penicillium glaucum,* Polyporus, such as *Polyporus versicolor,* Aureobasidium, such as *Aureobasidium pullulans,* Sclerophoma, such as *Sclerophoma pityophila,* Trichoderma, such as *Trichoderma viride,* Escherichia, such as *Escherichia coli,* Pseudomonas, such as *Pseudomonas aeruginosa* and Staphylococcus, such as *Staphylococcus aureus.*

Depending on the field of application, an active compound according to the invention can be converted into the customary formulations, such as solutions, emulsions, suspensions, powders, pastes and granules. These can be prepared in any known manner, for example, by mixing the active compounds with an extender, e.g., a liquid solvent and/or solid carriers, or, if desired, a surface-active agent such as an emulsifier and/or dispersing agent.

Liquid solvents for the active compounds may be water, alcohols, such as lower aliphatic alcohols, preferably ethanol or isopropanol, ketones, such as acetone or methyl ethyl ketone, liquid hydrocarbons, such as benzene fractions, and halogenated hydrocarbons, such as 1,2-dichloroethane.

The use concentrations of the active compounds according to the invention depend on the nature and the occurrence of the microorganisms to be combated, and on the composition of the material to be preserved. The optimum amount to be employed can be determined by means of series of tests. The use concentrations are in general in the range from 0.00005 (0.5 ppm) to 5% by weight, preferably from 0.0001 to 1.0%, relative to the material to be preserved.

In order to more fully illustrate the invention, attention is directed to the following examples:

EXAMPLE 1

Synthesis of Iodopropargyl Succinate

Procedure A: To a 1 liter reaction flask containing 250 ml of chloroform and 50 g of succinic anhydride (0.50 mol) was added a solution of 91 g of iodopropargyl alcohol (0.50 mol) in 250 ml of chloroform at <10° C. After completing the addition, 2 ml of triethylamine (0.02 mol) was added. The reaction mixture was allowed to warm up to room temperature and stirred at room temperature over the weekend (3 days). Thin layer chromatograph of the reaction mixture indicated disappearance of starting iodopropargyl alcohol. The entire reaction mixture was concentrated and dried to remove solvent. A light brown solid (145 g) was obtained (theory 141 g, crude yield quantitative).

The crude product was recrystallized from 250 ml of ethyl acetate to obtain 104.2 g of white powder (73.9% yield); mp 90°-92° C. Elemental analysis found (cal'd): C, 30.35 (29.79); H, 2.55 (2.48); I, 44.20 (45.03).

Procedure B: Into a 250 ml reaction flask equipped with a mechanical stirrer, a thermometer and an addition funnel was added 60 ml pyridine, 30 g (0.3 mol) of succinic anhydride and 1 drop of dibutyltin dilaurate.

To this slurry at about 10° C. was added a solution of 54.6 g iodopropargyl alcohol (0.30 mol) in 60 ml pyridine. The mixture was stirred at room temperature overnight. The resulting dark brown solution was poured over 150 ml of concentrated HCl in 200 g of ice. The organic material was extracted with three 150 ml portions of ethyl acetate. The combined extracts were filtered through 30 g of silica gel.

Upon removal of ethyl acetate and recrystallization from methylene chloride, 67.2 g of white crystalline was obtained (79.5% yield); mp 90° C. Elemental analysis, found (cal'd): C, 29.56 (29.79); H, 2.34 (2.48); I, 45.44 (45.03).

EXAMPLE 2

Synthesis of Iodopropargyl Phthalate

Into a 250 ml reaction flask equipped with a mechanical stirrer, a thermometer and an addition funnel was charged 22.2 g of phthalic anhydride (0.15 mol), 30 ml of pyridine, 1 drop of dibutyltin dilaurate, and a solution of 27.3 g of iodopropargyl alcohol (0.15 mol) in 30 ml of pyridine. The reaction was exothermic, and the temperature rose to 30° C. The mixture was heated to 50° C. for 1 hr and cooled to room temperature. The resulting brown solution was added to a mixture of 75 ml concentrated HCl over 150 g of ice. The organic material was extracted with three 150 ml portions of ethyl acetate.

The combined ethyl acetate solution was concentrated to a light beige colored solid, obtaining 44.2 g (theory 49.5 g, 89.2%) of iodopropargyl phthalate; mp 110°-112° C. Elemental analysis, found (cal'd): C, 40.26 (40.00); H, 2.08 (2.12); I, 37.90 (38.48).

EXAMPLE 3

Synthesis of Iodopropargyl Diglycolate

Into a 500 ml reaction flask equipped with a mechanical stirrer, a thermometer, and an addition funnel, was added 200 ml of pyridine and 58.0 g of diglycolic anhydride (0.50 mol). To the above stirred mixture at about 5° C. was added a solution of 91 g iodopropargyl alcohol (0.50 mol) in 100 ml of pyridine. After addition, the mixture was stirred at room temperature overnight. The resulting mixture was poured over a mixture of 350 ml concentrated HCl on 400 g of ice, and extracted with three 200 ml portions of ethyl acetate. The ethyl acetate solution was concentrated to about 200 ml and filtered through 30 g of silica gel.

Upon removal of solvent and drying under pump, a light beige colored solid was obtained, wt. 112.2 g (theory 149.0 g, 75%); mp 75° C. Elemental analysis, found (cal'd): C,28.22 (28.19); H, 2.39 (2.34); I, 42.49 (42.62).

EXAMPLE 4

Synthesis of Iodopropargyl Maleate

In a 500 ml reaction flask equipped with a mechanical stirrer, a thermometer and an addition funnel was added 24.5 g of maleic anhydride (0.25 mol) and 150 ml of chloroform. To the slurry was added a solution of 45.5 g of iodopropargyl alcohol (0.25 mol) in 100 ml of chloroform and 1 ml of triethylamine (0.01 mol). The mixture was stirred at room temperature overnight. The resulting light brown solution was filtered through 20 g of silica gel and concentrated to a pale yellow solid, wt. 63.6 g (theory 70.0 g, 91% yield).

This sample was recrystallized from ethyl acetate to obtain a white crystal; mp 72°-74° C. Elemental analysis, found (cal'd): C, 30.03 (30.00); H, 1.94 (1.79); I, 45.28 (45.36).

EXAMPLE 5

Synthesis of Iodopropargyl Itaconate

In a 1 liter reaction flask equipped with a mechanical stirrer, a thermometer and an addition funnel was added 56 g of itaconic anhydride (0.46 mol), 250 ml of chloroform, and a solution of 83.7 g of iodopropargyl alcohol (0.46 mol) in 250 ml of chloroform. Thereafter, 2 ml of triethylamine was added and the solution stirred at room temperature overnight. The resulting dark, clear solution was filtered through 30 g of silica gel and the solvent removed to obtain 112 g of semi-solid (80.2% yield).

This material was recrystallized from chloroform and formed white crystals; mp 95°-97° C. Elemental analysis, found (cal'd): C, 32.60 (32.65); H, 2.33 (2.38); I, 43.30 (43.20).

EXAMPLE 6

Synthesis of Iodopropargyl Tetrachlorophthalate

Into a 1 liter reaction flask containing 200 ml of chloroform was added 85.8 g (0.30 mol) of tetrachlorophthalic anhydride, a solution of 54.6 g iodopropargyl alcohol (0.30 mol) in 200 ml of chloroform, and 2 ml of triethylamine (0.02 mol). The mixture was stirred at room temperature overnight and filtered.

The filtrate was concentrated to dryness, obtaining 124.5 g of iodopropargyl tetrachlorophthalate (theory 139.8 g, 88.9%). Elemental analysis, found (cal'd): C, 27.66 (28.20); H, 0.68 (0.64); I, 28.43 (27.14); Cl 28.30 (30.34).

EXAMPLE 7

Synthesis of Chlorhexidine Iodopropargyl Diglycolate 1.01 g of chlorhexidine base (99.9% pure, 2.00 mmol) was suspended in 49 g of anhydrous ethanol in an 8 oz bottle. With stirring, 1.192 g of iodopropargyl diglycolate (4.00 mmol) was added. The mixture gradually became a clear solution in <5 min. Distilled water (48.8 g) was added to bring the total contents to 100 g.

This formed a chlorhexidine iodopropargyl diglycolate solution, containing 1.2% active iodopropargyl diglycolate.

EXAMPLE 8

Microbiocidal Activity

Time studies were performed on six iodopropargyl compounds of the invention in the sodium salt form at 1,000 ppm against five organisms at 5 different time intervals. The chemical structure of the first five compounds are seen in Table I. The sixth compound is a salt made from chlorhexidine base and iodopropargyl diglycolate.

TABLE I

Mono-Iodopropargyl Esters of Dicarboxylic Anhydrides

Iodopropargyl Succinate

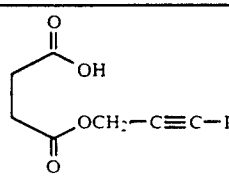

TABLE I-continued

Mono-Iodopropargyl Esters of Dicarboxylic Anhydrides

Iodopropargyl Phthalate

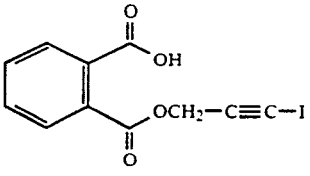

Iodopropargyl Diglycolate

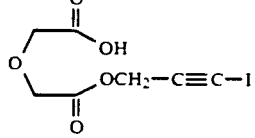

Iodopropargyl Maleate

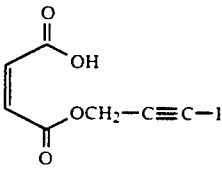

Iodopropargyl Itaconate

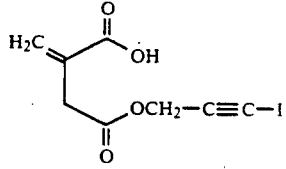

The efficacy data are summarized in Table II. IPBC was used as a control. The data for two solvents (ethanol and water) and inoculum are also presented for comparison. Each test preparation was inoculated with one of five microbial suspensions. The concentration in the test preparation immediately after inoculation was between 100,000 and 1,000,000 microorganisms per ml and the test results are indicated as organisms/ml. TNTC means too numerous to count.

TABLE II

| Test Organism | Contact Time | | | | |
|---|---|---|---|---|---|
| | 1 Hour | 24 Hours | 48 Hours | 72 Hours | 7 Days |
| Sodium Iodopropargyl Succinate | | | | | |
| A. niger | $1 \times 10^5$ | $6 \times 10^4$ | <10 | <10 | <10 |
| C. albicans | $8 \times 10^5$ | <10 | <10 | <10 | <10 |
| Ps. aeruginosa | $3 \times 10^5$ | <10 | <10 | <10 | <10 |
| S. marcescens | $3.6 \times 10^6$ | <10 | <10 | <10 | <10 |
| P. vulgaris | $3 \times 10^4$ | <10 | <10 | <10 | <10 |
| Sodium Iodopropargyl Phthalate | | | | | |
| A. niger | $2.4 \times 10^4$ | $1 \times 10^6$ | $1.5 \times 10^4$ | <10 | <10 |
| C. albicans | $6 \times 10^5$ | <10 | $1.3 \times 10^4$ | $1.6 \times 10^3$ | <10 |
| Ps. aeruginosa | $7 \times 10^5$ | <10 | <10 | <10 | <10 |
| S. marcescens | $4.1 \times 10^6$ | <10 | $7 \cdot 10^2$ | <10 | <10 |
| P. vulgaris | <10 | <10 | <10 | <10 | <10 |
| Sodium Iodopropargyl Diglycolate | | | | | |
| A. niger | $1.7 \times 10^5$ | $6 \times 10^4$ | <10 | <10 | <10 |
| C. albicans | $3 \times 10^5$ | <10 | <10 | <10 | <10 |
| Ps. aeruginosa | $8 \times 10^4$ | <10 | <10 | <10 | <10 |
| S. marcescens | $2 \times 10^6$ | <10 | <10 | <10 | <10 |
| P. vulgaris | $5 \times 10^4$ | <10 | <10 | <10 | <10 |
| Sodium Iodopropargyl Maleate | | | | | |
| A. niger | $2 \times 10^4$ | $1.6 \times 10^5$ | <10 | <10 | <10 |
| C. albicans | $4 \times 10^5$ | <10 | <10 | <10 | <10 |
| Ps. aeruginosa | $5 \times 10^5$ | <10 | <10 | <10 | <10 |
| S. marcescens | $2.1 \times 10^6$ | <10 | <10 | <10 | <10 |
| P. vulgaris | $3 \times 10^4$ | <10 | <10 | <10 | <10 |
| Sodium Iodopropargyl Itaconate | | | | | |
| A. niger | $1.5 \times 10^4$ | $5 \times 10^5$ | <10 | <10 | <10 |
| C. albicans | $7 \times 10^5$ | <10 | <10 | <10 | <10 |
| Ps. aeruginosa | $1.9 \times 10$ | <10 | <10 | <10 | <10 |
| S. marcescens | $2.9 \times 10^6$ | <10 | <10 | <10 | <10 |
| P. vulgaris | <10 | <10 | <10 | <10 | <10 |
| Chlorhexidine Iodopropargyl Diglycolate | | | | | |
| A. niger | $6 \times 10^4$ | $1.1 \times 10^4$ | <10 | <10 | <10 |
| C. albicans | <10 | <10 | <10 | <10 | <10 |
| Ps. aeruginosa | <10 | <10 | <10 | <10 | <10 |
| S. marcescens | <10 | <10 | <10 | <10 | <10 |
| P. vulgaris | <10 | <10 | <10 | <10 | <10 |
| IPBC (control) | | | | | |
| A. niger | <10 | <10 | <10 | <10 | <10 |
| C. albicans | $6.8 \times 10^4$ | <10 | <10 | <10 | <10 |
| Ps. aeruginosa | $6 \times 10^5$ | <10 | $3.5 \times 10^5$ | $3.9 \times 10^3$ | $1 \times 10^5$ |
| S. marcescens | $1.1 \times 10^6$ | <10 | <10 | $5.6 \times 10^6$ | $8 \times 10^4$ |
| P. vulgaris | <10 | <10 | <10 | <10 | $7.2 \times 10^5$ |
| Ethanol (4%, control) | | | | | |
| A. niger | $5 \times 10^5$ | $3 \times 10^6$ | $1 \times 10^6$ | $5 \times 10^6$ | $1.3 \times 10^6$ |
| C. albicans | $6 \times 10^5$ | $2 \times 10^5$ | $1.9 \times 10^6$ | $1.8 \times 10^6$ | $1.6 \times 10^6$ |
| Ps. aeruginosa | $3 \times 10^6$ | $5 \times 10^4$ | TNTC | $4 \times 10^7$ | $8 \times 10^6$ |
| S. marcescens | $2 \times 10^6$ | $1.8 \times 10^6$ | $2 \times 10^7$ | TNTC | $2.2 \times 10^6$ |
| P. vulgaris | $1.2 \times 10^5$ | $3 \times 10^4$ | TNTC | $1 \times 10^5$ | $2.5 \times 10^6$ |

TABLE II-continued

| Test Organism | Contact Time | | | | |
|---|---|---|---|---|---|
| | 1 Hour | 24 Hours | 48 Hours | 72 Hours | 7 Days |
| Water (control) | | | | | |
| A. niger | $3 \times 10^5$ | $5 \cdot 10^6$ | $4 \times 10^6$ | $5 \times 10^6$ | $7 \times 10^5$ |
| C. albicans | $1 \times 10^6$ | $3 \cdot 10^6$ | $2.4 \times 10^6$ | $5 \times 10^6$ | $4 \times 10^6$ |
| Ps. aeruginosa | $2.8 \times 10^6$ | $3 \times 10^5$ | TNTC | $1.1 \times 10^8$ | $1.1 \times 10^9$ |
| S. marcescens | $3 \times 10^6$ | $2 \times 10^7$ | $1.7 \times 10^8$ | TNTC | $1.2 \times 10^8$ |
| P. vulgaris | $6 \times 10^5$ | $2.3 \times 10^5$ | TNTC | $2.3 \times 10^6$ | $1.3 \times 10^7$ |
| Inoculum | | | | | |
| A. niger | $2 \times 10^7$ | | | | |
| C. albicans | $2 \times 10^8$ | | | | |
| Ps. aeruginosa | $3 \times 10^8$ | | | | |
| S. marcescens | $3 \times 10^7$ | | | | |
| P. vulgaris | $5 \times 10^7$ | | | | |

The above data show that Compounds 1, 3, 4, 5, and 6 are equal in microbiological activity, showing activity against C. albicans, Ps. Aeruginosa, S. marcescens and P. vulgaris in 24 hours and against A. niger in 48 hours. With the exception of iodopropargyl phthalate, the compounds of the invention also show better bactericidal activity than IPBC while maintaining an acceptable level of fungicidal activity.

EXAMPLE 9

Formulations

To demonstrate the ease of formulation of the compounds of the instant invention, 50 g of an unpreserved shampoo was admixed with 0.1 g of a 10% solution of sodium iodopropargyl succinate and 0.01 g of IPBC (Polyphase P100, TM of Troy), an off-white granular powder. The succinate solution blended immediately with the shampoo at room temperature, resulting in a clear shampoo solution. On the other hand, even the small amount of the IPBC remained undissolved after 2 hours of stirring. The unpreserved shampoo contained the following ingredients:

| Sodium lauryl ether sulfate | 21.7 parts |
|---|---|
| Triethanol amine lauryl sulfate | 16.3 parts |
| Cocamide | 3.0 parts |
| Water | 59.0 parts |
| Citric acid | qs pH = 7 |

EXAMPLE 10

Light Stability

This example presents a qualitative measurement of light stability of the compounds of the invention and IPBC. Borosilicate bottles containing test solutions were placed in front of fluorescent light at room temperature. The APHA color of the solution was measured periodically. Solutions of 2.5% of iodopropargyl compounds in water were prepared. The IPBC, not being water-soluble, was tested in ethanol.

TABLE III

| | APHA Color | | | | |
|---|---|---|---|---|---|
| Sample | Week 0 | Week 1 | Week 2 | Week 3 | Week 7 |
| IPBC | 0 | 10 | 90 | 225 | 300 |
| IP Succinate (Na salt) | 5 | 5 | 5 | 5 | 5 |
| IP Phthalate (Na salt) | 10 | 10 | 10 | 10 | 10 |
| IP Diglycolate (Na salt) | 10 | 10 | 10 | 10 | 10 |
| IP Maleate (Na salt) | 10 | 40 | 40 | 50 | 10 |
| IP Itaconate (Na salt) | 15 | 60 | 60 | 60 | 100 |

The above data show that the sodium salt of the iodopropargyl compounds of the invention had much better light stability than IPBC.

What is claimed is:

1. A compound having one of the following formulas:

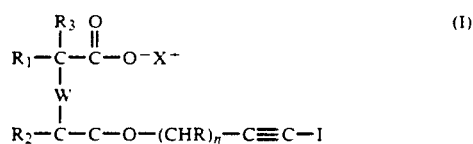

(I)

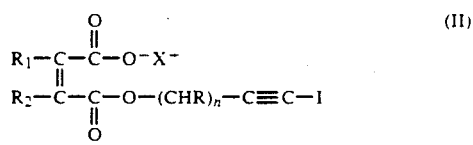

(II)

wherein

R is hydrogen or methyl;

n is 1 to 16;

$R_1$ and $R_2$ are defined as $R_3$ and $R_4$ below or where the compound is of formula (I) above and W is a single bond are joined to form a cycloalkyl or a cycloalkenyl group or where the compound is of formula (II) above are joined to form an aromatic or a haloaromatic group;

$R_3$ and $R_4$ are independently selected from hydrogen, alkyl, cycloalkyl, alkenyl, cycloalkenyl, aryl, a haloaryl group;

W may be a single bond, oxygen, $NR_5$, or $C(CH_3)_2$, wherein $R_5$ is an amino substituted alkyl group; and X is hydrogen or a salt-forming cation.

2. The compound of claim 1 wherein the salt-forming cation is an alkali metal, an alkaline earth metal, an ammonium, a tertiary ammonium, a quaternary ammonium, a biguanide or a polybiguanide.

3. Iodopropargyl succinate.

4. Iodopropargyl phthalate.

5. Iodopropargyl diglycolate.

6. Iodopropargyl maleate.

7. Iodopropargyl itaconate.

8. Chlorhexidine iodopropargyl diglycolate.

9. A process for preparing a mono-iodoalkenyl ester of a dicarboxylic acid anhydride which comprises reacting equimolar quantities of an iodoalkynyl alcohol having from 3 to 6 carbon atoms with a dicarboxylic acid anhydride in the presence of a catalytic amount of a tertiary amine in a non-alcoholic organic solvent.

10. The process of claim 9 wherein the alcohol is iodopropargyl alcohol.

11. The process of claim 9 wherein the dicarboxylic acid anhydride is succinic anhydride itaconic, anhydride, phthalic anhydride, tetrachlorophthalic anhydride, diglycolic anhydride, maleic anhydride, dichloromaleic anhydride, cis-5-norbornene-endo-2,3-dicarboxylic anhydride, 3,3-dimethylglutaric anhydride, ethylenediamine tetraacetic dianhydride, s-acetylmercaptosuccinic anhydride and 2-dodecen-1-yl succinic anhydride.

12. The process of claim 9 wherein the anhydride is a saturated or aromatic compound, the solvent is a tertiary amine and the temperature of reaction is from $-20°$ to $100°$ C.

13. The process of claim 9 wherein the solvent is a tertiary amine.

14. The process of claim 9 wherein the solvent is triethylamine.

15. The process of claim 9 wherein the anhydride contains olefinic unsaturation and the temperature of the reaction is room temperature.

16. The process of claim 15 wherein the solvent is a halogenated organic compound.

17. The process of claim 9 wherein the tertiary amine is triethylamine or pyridine.

18. A microbiocidal composition comprising a microbiocidally effective amount of the compound of claim 1 and an adjuvant.

19. A process of killing microorganisms which comprises contacting said microorganisms with a biocidally effective amount of the compound of claim 1.

* * * * *